(12) United States Patent
Barrall

(10) Patent No.: US 10,980,586 B2
(45) Date of Patent: Apr. 20, 2021

(54) DRIVER DEVICE WITH ANTI-ROTATION FEATURE

(75) Inventor: Benjamin S. Barrall, Conshohocken, PA (US)

(73) Assignee: DePuy Synthes Products, Inc., New Brunswick, NJ (US)

( * ) Notice: Subject to any disclaimer, the term of this patent is extended or adjusted under 35 U.S.C. 154(b) by 713 days.

(21) Appl. No.: 13/047,387

(22) Filed: Mar. 14, 2011

(65) Prior Publication Data

US 2012/0239095 A1    Sep. 20, 2012

(51) Int. Cl.
*A61B 17/86*    (2006.01)
*A61B 17/16*    (2006.01)
*A61B 17/88*    (2006.01)
*A61B 90/00*    (2016.01)

(52) U.S. Cl.
CPC .......... *A61B 17/86* (2013.01); *A61B 17/1655* (2013.01); *A61B 17/8875* (2013.01); *A61B 17/162* (2013.01); *A61B 17/1633* (2013.01); *A61B 17/1671* (2013.01); *A61B 17/864* (2013.01); *A61B 17/8872* (2013.01); *A61B 2090/035* (2016.02); *A61B 2090/062* (2016.02)

(58) Field of Classification Search
CPC .............. A61B 17/1655; A61B 17/864; A61B 17/8875; A61B 17/162; A61B 17/1671; A61B 2019/305; A61B 17/1796; A61B 17/1778; A61B 17/1714; A61B 17/1633; A61B 17/8872; A61B 17/1757; A61B 17/171; A61B 17/17; A61B 17/8866

USPC ....... 606/80, 104, 96, 79, 87, 180, 311, 312; 408/192–193, 202–204, 241, 186, 110, 408/118

See application file for complete search history.

(56) References Cited

U.S. PATENT DOCUMENTS

| | | | | |
|---|---|---|---|---|
| 3,115,168 A | * | 12/1963 | Acres | 81/451 |
| 3,190,046 A | * | 6/1965 | Bryant | 451/374 |
| 4,040,327 A | * | 8/1977 | Otaki | 411/423 |
| 4,517,865 A | * | 5/1985 | Huang | 81/475 |
| 5,049,150 A | * | 9/1991 | Cozad | A61B 17/8866 606/80 |
| 5,250,055 A | * | 10/1993 | Moore et al. | 606/148 |
| 5,423,824 A | * | 6/1995 | Akerfeldt | A61B 10/025 600/567 |
| 5,474,558 A | * | 12/1995 | Neubardt | A61B 17/8875 600/554 |
| 5,643,274 A | * | 7/1997 | Sander | A61B 17/1633 606/104 |

(Continued)

*Primary Examiner* — Marcela I. Shirsat
(74) *Attorney, Agent, or Firm* — Meunier Carlin & Curfman LLC

(57) ABSTRACT

Disclosed is an axial and rotational stopping device for use when creating threads in a predrilled pilot hole or inserting an allograft bony void filler or synthetic implant into a threaded hole. The device can also provide consistent depth control for drilling a pilot hole, tapping the hole to create threads, and implanting an allograft bony void filler or synthetic implant while preventing damage to the threads in the tapped hole that would be caused by continuing to rotate a tap once the depth stop has been reached and the tap can no longer advance in the axial direction, as well as preventing damage to the threads in the tapped hole, the threads on the mating allograft bony void filler or synthetic implant, and the drive features on either the driver instrument or the allograft bony void filler or synthetic implant.

17 Claims, 9 Drawing Sheets

(56) References Cited

U.S. PATENT DOCUMENTS

| | | | | |
|---|---|---|---|---|
| 6,095,020 | A * | 8/2000 | Rinner | B25B 15/02 81/475 |
| 6,951,562 | B2 * | 10/2005 | Zwirnmann | A61B 17/1633 606/80 |
| 7,013,769 | B2 * | 3/2006 | Chen | B25B 15/02 81/467 |
| 7,033,363 | B2 * | 4/2006 | Powell | A61B 17/1615 606/104 |
| 7,141,074 | B2 * | 11/2006 | Fanger | A61B 17/1617 606/80 |
| 2005/0097994 | A1 * | 5/2005 | Liao | B25B 13/466 81/58.3 |
| 2006/0126822 | A1 * | 6/2006 | Schmidt | H04M 9/082 379/406.01 |
| 2006/0236822 | A1 * | 10/2006 | Nish | 81/125 |
| 2010/0030218 | A1 * | 2/2010 | Prevost | A61B 17/1655 606/80 |
| 2012/0010659 | A1 * | 1/2012 | Angert | A61B 17/1757 606/247 |
| 2012/0118333 | A1 * | 5/2012 | Piccioni | A46B 17/06 134/33 |

* cited by examiner

100

150

DRIVER DEVICE WITH ANTI-ROTATION FEATURE

BACKGROUND

Vertebral fixation (a.k.a. spinal fixation) is a neurosurgical procedure in which two or more vertebrae are anchored to each other through a synthetic vertebral fixation device. The purpose of the vertebral fixation device is to reduce vertebral mobility in order to mitigate the risk of damage to the spinal cord or spinal roots. A vertebral fixation procedure may provide relief from vertebral deformity, degenerative vertebral disorders (such as spondylolisthesis), or vertebral fractures.

Vertebral disorders are being treated more and more often using minimally invasive posterior transpedicular or extrapedicular approaches to emplace spinal implant devices. The most common vertebral fixation devices use some form of threaded shaft (i.e., a screw) to achieve stable fixation. For spinal fusions, on the other hand, the implantation of an allograft bony void filler (or "allograft dowel") has proven to be effective. However, the use of threaded allograft bony void fillers or synthetic implants, as well as the implantation of allograft bony void fillers or synthetic implants into threaded holes created in bony structures, present several challenges with regard to controlling the rotational forces concurrent with controlling the axial forces applied during such procedures.

SUMMARY

Various embodiments herein disclosed are directed to an axial and rotational stopping device. Certain embodiments provide axial and rotational stopping of a tap when creating threads in a predrilled pilot hole. Other embodiments provide axial and rotational stopping of an allograft bony void filler or synthetic implant into the threaded hole. Several embodiments provide consistent depth control for drilling a pilot hole, tapping the hole to create threads, and implanting an allograft bony void filler or synthetic implant. Such embodiments prevent damage to the threads in the tapped hole that would be caused by continuing to rotate a tap once the depth stop has been reached and the tap can no longer advance in the axial direction. Additionally, this will prevent damage to the threads in the tapped hole, the threads on the mating allograft bony void filler or synthetic implant or the drive features on either the driver instrument or the allograft bony void filler or synthetic implant.

In addition, several embodiments are directed to a two-part device comprising mating toothed surfaces that, when engaged, prevent rotation in one direction while allowing rotation in the opposite direction. For certain embodiments, the two-part device may comprise a driven (male) shaft and a stationary (female) guide tube surrounding the male shaft. For those embodiments where a relative clockwise or right-handed rotation results in an axial advancement of a threaded component into a threaded hole or a tapping component into a predrilled pilot hole, the mating toothed surfaces act to prevent relative clockwise or right-handed rotation when engaged, such as at the point where the instruments have reached the appropriate depth. Several embodiments are directed to applications where axial positioning is a higher priority than the torque applied to a threaded instrument, allograft bony void filler, or synthetic implant.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE DRAWINGS

To facilitate an understanding of and for the purpose of illustrating the present disclosure, exemplary features and implementations are disclosed in the accompanying drawings, it being understood, however, that the present disclosure is not limited to the precise arrangements and instrumentalities shown, and wherein similar reference characters denote similar elements throughout the several views, and wherein.

DETAILED DESCRIPTION

Figure 1A:
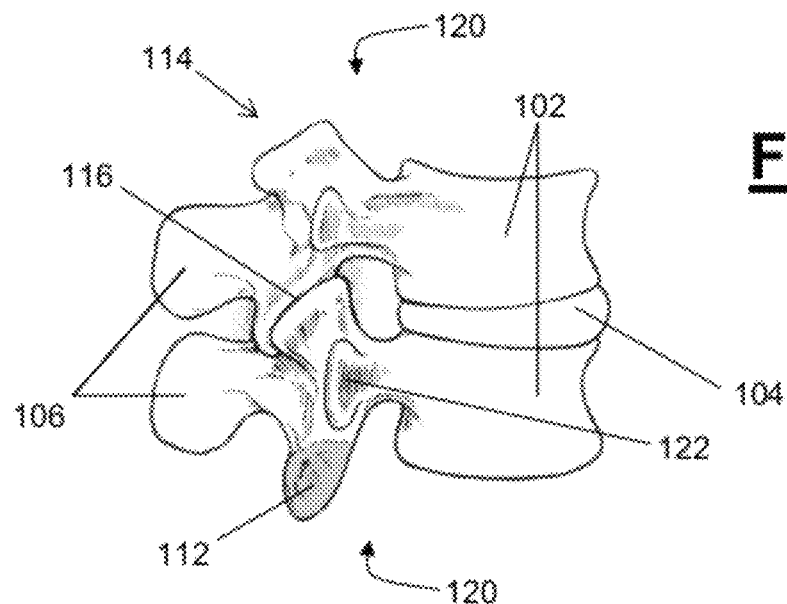
FIG. 1A is an illustration of an exemplary bony structure—specifically, two adjacent vertebra—for which several embodiments herein disclosed may be utilized.

Creating a threaded hole in bony anatomy, and subsequently emplacing an allograft bony void filler or synthetic implant into the threaded hole, presents several challenges. For example, when a drill is used to create pilot hole, the surgeon (or the tool that the surgeon may use) creates torque about the longitudinal axis of the drill to generate rotary cutting motion which, in turn, removes bony material to form a relatively smooth-walled hole. The surgeon also applies some axial force to the drill while it is rotating in order to obtain the target depth for the hole in the bony structure. When drilling the hole, however, the surgeon does not want the tip of the drill to advance beyond a certain point, such as when drilling into the facet joints of two vertebrae of a spinal column during in a spinal fusion procedure and risking damage to the spinal cord. In these situations, one approach is to incorporate an axial stop to prevent unintended advancement of the drill bit.

Similarly, when a typical tap instrument is used to create helical threading in a pre-drilled pilot hole, the surgeon (or the tool that he uses) also applies torque about the longitudinal axis of the tap to generate rotary motion which, in turn, causes the threaded cutting surfaces of the tap to bite into the walls of the pre-drilled hole. However, the surgeon once again applies some axial force to the tap while rotating it, this time to help start the tap into the hole. Of course, once the threaded surfaces of the tap have advanced sufficiently into the pre-drilled hole, the amount of axial force applied to the tap can be reduced as the helical geometry of the tap threads will draw the instrument deeper into the pre-drilled hole as the surgeon generates additional rotary motion. One approach, when tapping a blind hole (or whenever there is a risk of the tap advancing beyond a certain point), is to incorporate an axial stop to prevent unintended advancement of the tip beyond the depth of the predrilled hole.

With regard to a tap, however, a simple axial stop (such as one used for drilling) may introduce new problems, namely, if the tap is constrained from advancing deeper into the hole then additional rotary motion will cause the threaded cutting geometry of the tap (which is typically made of stronger material than the bony structure being tapped) to remove or strip the newly created threads in the bony structure, resulting in reduced or no retention of the threaded member that is intended to be placed into the hole. Therefore, not only does axial advancement need to be limited, but also the rotational force needs to be correspondingly constrained.

Even when the drilling and tapping are successful, however, there are yet additional challenges when driving a threaded allograft bony void filler or synthetic implant into a blind, bony, tapped hole. Without benefit of an axial stop, it is possible to drive the allograft or implant until it bottoms out on the bottom of the hole. At this point, if additional rotation is applied to the allograft or implant, several outcomes may occur. First, if the threads on the driven allograft or implant are stronger than those in the bony tapped hole, then the additional rotational force will damage or destroy the threads in the bony tapped hole. Conversely, if the threads in the tapped hole are stronger than the threads on the driven allograft or implant, then the additional rotational force will damage or destroy the threads on the allograft or implant. Both of these scenarios will result in reduced or no retention of the threaded allograft or implant. In addition, the instrument used to drive the allograft bony void filler or synthetic implant into the tapped hole could damage the mating drive features on the allograft or implant or, conversely, the drive feature on the driving instrument could itself be damaged by the allograft or implant. Finally, all of the aforementioned scenarios could make it difficult to remove the allograft or implant from the hole if attempted during the procedure or after.

One approach for addressing the issues described above calls for the surgeon to "feel" or "sense" an increase in the torque required to advance the tap when the tap reaches the bottom of the pilot hole. However, such tactile sensing can be difficult in bony anatomy because differences in bone density or strength could produce false cues as the tap is advanced into the predrilled pilot hole. In addition, weak or osteoporotic bone may strip or fail before an appreciable increase in torque is achieved.

Another approach for controlling the rotational forces and/or displacement when, for example, driving a threaded allograft or implant involves the use of torque limiting or indicating instruments which will either prevent the surgeon from applying too much torque or provide the surgeon with a measurement of the torque that he/she is applying to the graft or implant. Such devices are commonly utilized in other situations to create a pre-stressed condition in other threaded components (e.g., tension in a bolt, or radial forces in a conical locking thread) in order to prevent loosening or to apply required compressive loads between fastened elements. For threaded allografts or implants, it seems reasonable that these mechanisms could also be used to prevent damage to the threaded components in the system. However, the problem with these devices is that they rely on an accurate quantification of the torsional strength of the threaded components as well as the torques required to drive the threaded components into a substrate (e.g. bone). Unfortunately, it is entirely possible that extremely dense bone could cause premature tripping of a torque limiting device or provide a misleading torque measurement on a torque indicating device, thereby preventing the surgeon from applying correct torque or axial displacement to the threaded member. It is also possible that weak (e.g., osteoporotic) bone may strip before the limits of a torque limiting device are reached, and variations in the density and strength of the allograft tissue may lead to a situation where the drive feature on the graft strips before the limit of the torque limiting device is reached.

Disclosed herein are methods and devices that address the challenges inherent to situations where controlling the axial insertion depth of a tap or allograft bony void filler or synthetic implant is higher priority than applying a prescribed amount of torque to the threaded member. Several embodiments are directed to methods and devices for preventing relative rotational motion between a shaft (e.g. tap or driver) and a tube (e.g. a guide tube) as well as axial depth control. Certain of these embodiments are directed to achieve precise depth control of a tap tip and threaded allograft bony void filler or synthetic implant irrespective of the properties of the patient's bony anatomy, the torque required to insert the threaded member, or the torsional strength of the threaded member. For a threaded allograft bony void filler, this is especially attractive since variability in the mechanical properties of the patients bony anatomy and variability in the mechanical properties of the allograft due to donor bone quality and the effects of post-harvest processing generally make accurate quantification of the torque requirements difficult. Thus, for several embodiments, as the driven component is rotated into its final axial position, the opposing radial faces of the anti-rotation features will come into contact with one another, preventing relative rotation between the driven and the stationary component and effectively limiting the axial insertion depth of the driven component into the stationary component.

Figure 1B:
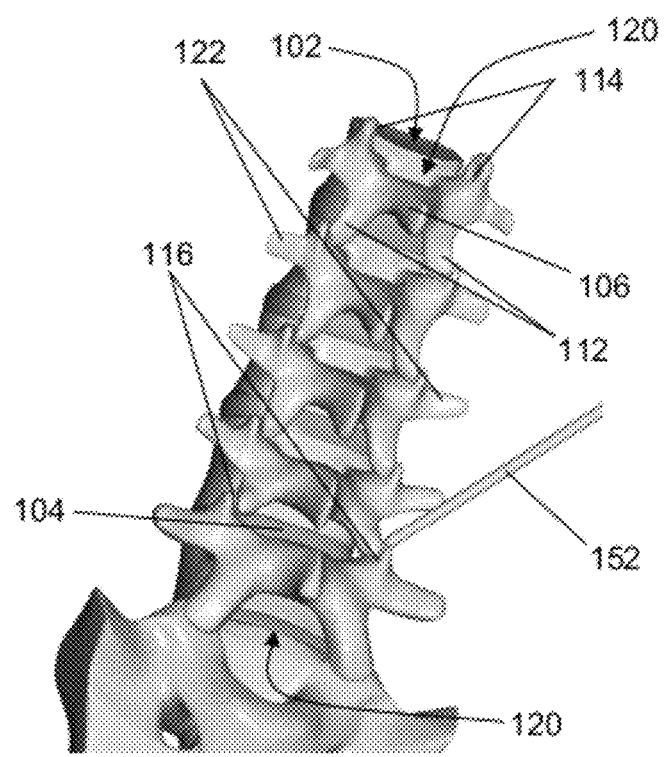
FIG. 1B is an illustration of a vertebral column, similar to that of FIG. 1A, but further showing an approach for placing an allograft bony void filler or synthetic implant into the threaded hole to fuse a facet joint.
Figure 2A:
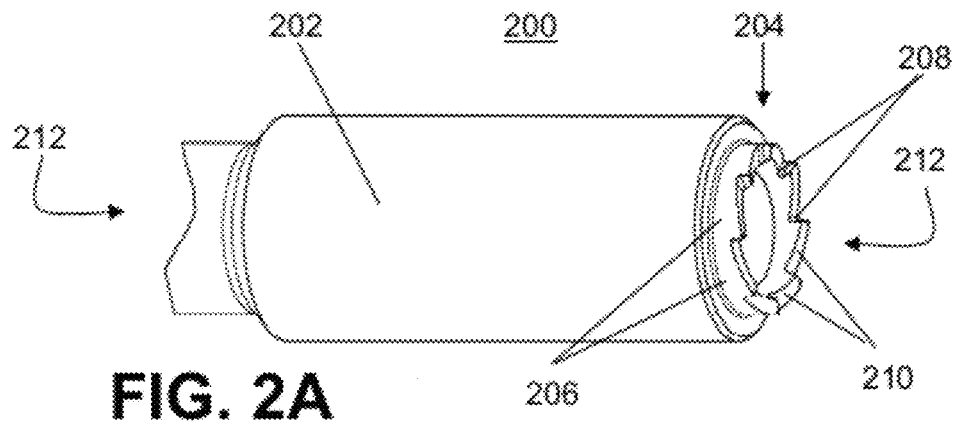
FIG. 2A is a partial three-dimensional view of the stationary (female) member of an axial and rotational stop device representative of several embodiments disclosed herein.
Figure 2B:
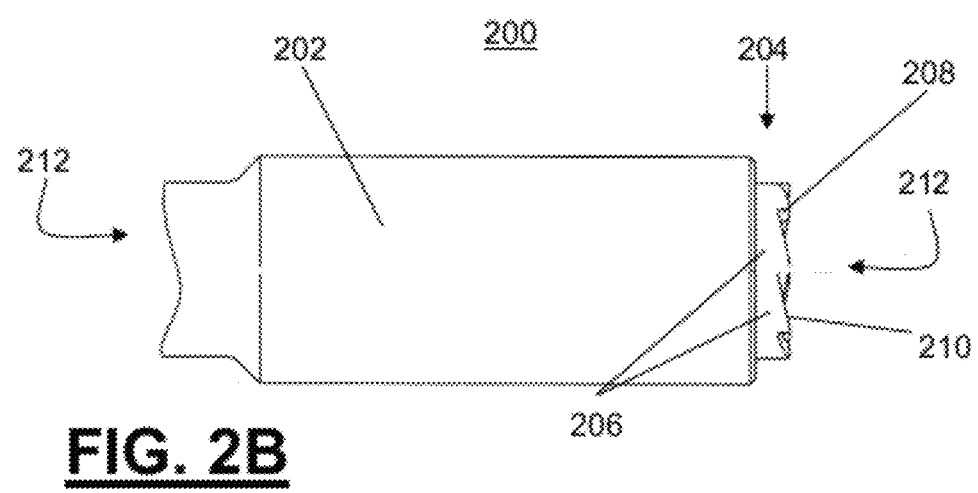
FIG. 2B is a partial side view of the stationary (female) member of the axial and rotational stop device of FIG. 2A.
Figure 2C:
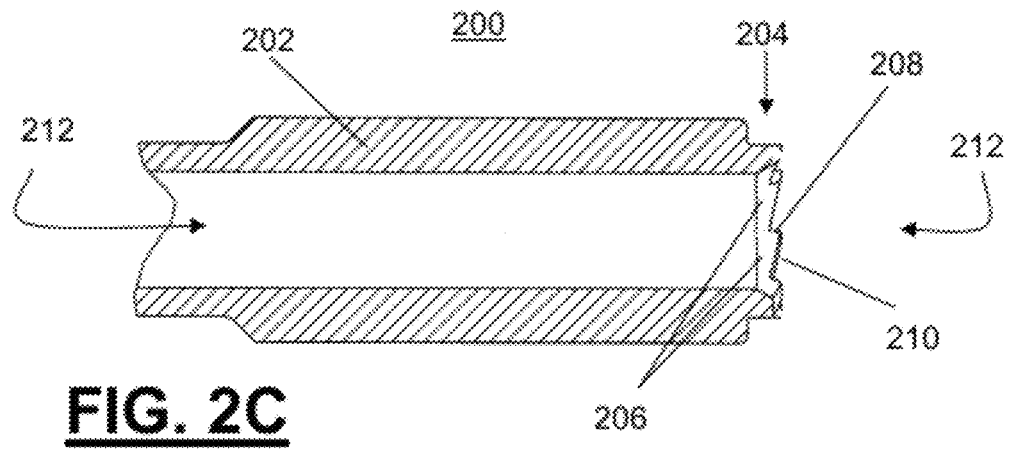
FIG. 2C is a partial cross-sectional view of the stationary (female) member of the axial and rotational stop device of FIGS. 2A and 2B.
Figure 2D:
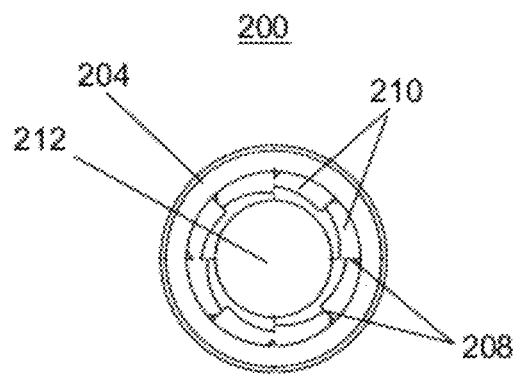
FIG. 2D is a partial end view of the stationary (female) member of the axial and rotational stop device of FIGS. 2A, 2B, and 2C.

FIG. 1A is an illustration of an exemplary bony structure—specifically, two adjacent vertebra 100—for which several embodiments herein disclosed may be utilized. FIG. 1B is an illustration of a vertebral column 150, similar to that of FIG. 1A, but further showing an approach for placing an allograft bony void filler or synthetic implant into the threaded hole to fuse a facet joint. Referring to the figures, each vertebrae comprises vertebral bodies 102 separated by intervertebral discs 104. The spinal cord (not shown) is protected within the spinal canal 120 behind the vertebral bodies 102. Each vertebrae further comprises spinous processes 106, transverse processes 122, and facet joints 116 between lower articular processes 112 and upper articular processes 114. In FIG. 1B, also shown is a guide pin that may be used to establish the trajectory for implantation of the allograft dowel or synthetic implantation device 152 for fusing a facet joint 116.

For several embodiments disclosed herein, the axial and rotational stop device comprises a stationary member and a driven member. The stationary member would be stationed on the proximal surface of the bony anatomy into which the threaded member(s) are being driven. The driven member could either be threaded itself or be used to drive a threaded allograft bony void filler or synthetic implant. Significantly, although numerous embodiment shown herein are for an application where the driven member features right-handed threads and the anti-rotation feature is intended to limit rotation when a clockwise torque is applied to the driven member, alternative embodiments may be directed to left-handed, counterclockwise versions in each instance herein disclosed.

FIGS. 2A, 2B, 2C, and 2D are a (partial) three-dimensional view, side view, cross-sectional view, and end view (respectively) of the stationary (female) member 200 of an axial and rotational stop device (the "stop device") representative of several embodiments disclosed herein. In the figures, the stationary member 200 comprises a hollow shaft 202 coupled to a mating toothed surface 204. The mating toothed surface 204 further comprises a plurality of proximal teeth 206 having a longitudinal surface 208 and a pitched surface 210. The hollow shaft 202 and mating toothed surface 204 together circumferentially bound a longitudinal hollow 212.

Figure 3A:
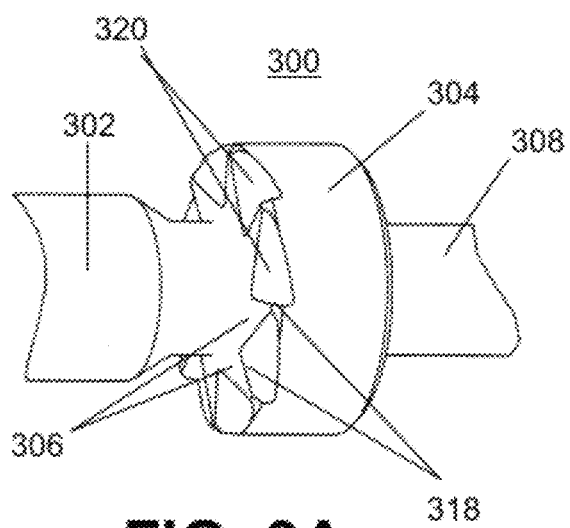
FIG. 3A is a partial three-dimensional view of the driven (male) member of an axial and rotational stop device representative of several embodiments disclosed herein.
Figure 3C:
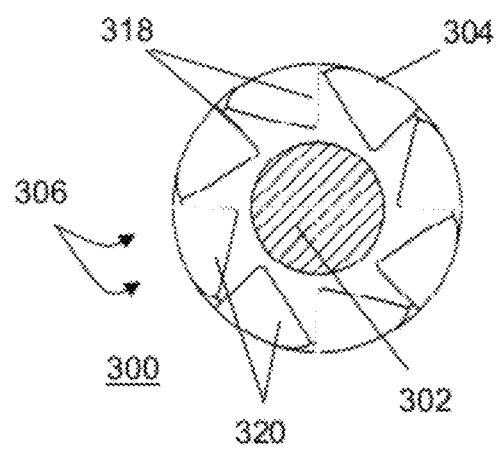
FIG. 3C is a partial end view of the driven (male) member of the axial and rotational stop device of FIGS. 3A and 3B.
Figure 3B:
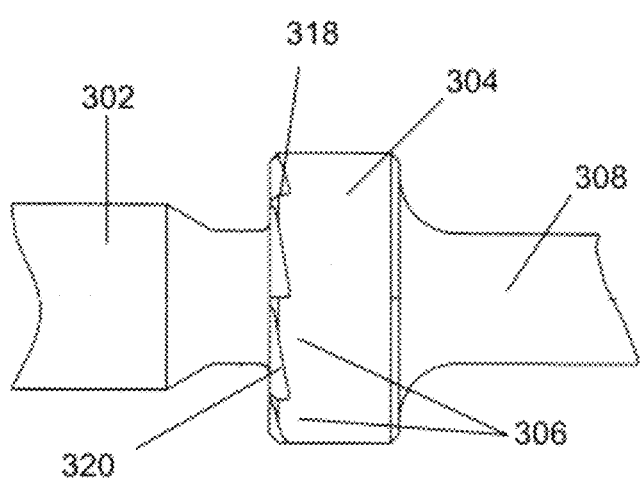
FIG. 3B is a partial side view of the driven (male) member of the axial and rotational stop device of FIG. 3A.

FIGS. 3A, 3B, and 3C are a (partial) three-dimensional view, side view, and end view (respectively) of the driven (male) member 300 of an axial and rotational stop device (the "stop device") representative of several embodiments disclosed herein. In the figures, the driven member 300 comprises a solid insertion shaft 302 coupled to mating toothed collar 304 coupled to a solid extension shaft 308. The mating toothed collar 304 further comprises a plurality of distal teeth 306 for engaging the proximal teeth 206 of the stationary member 200, where the distal teeth 306 have a longitudinal surface 318 and a pitched surface 320. Moreover, the solid insertion shaft 302 comprises a diameter sufficient to traverse the longitudinal hollow 212 of the stationary member 200, whereas the mating toothed collar 304 comprises a diameter greater than the diameter of the longitudinal hollow 212 of the stationary member 200.

Figure 4A:
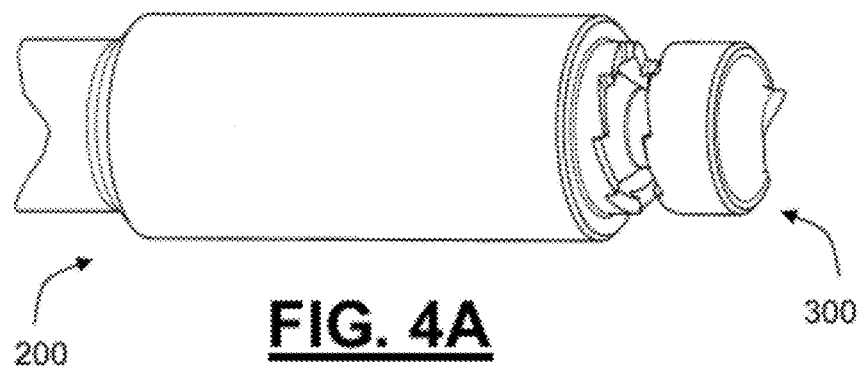
FIG. 4A is a partial three-dimensional view of the driven member and the stationary member operatively coupled together in an intermediate state representative of several embodiments disclosed herein.
Figure 4B:
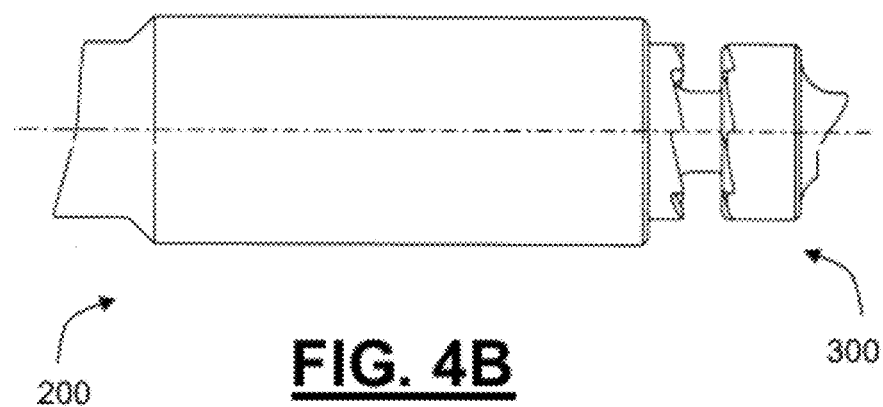
FIG. 4B is a partial side view of the driven member and the stationary member of FIG. 4A.
Figure 4C:
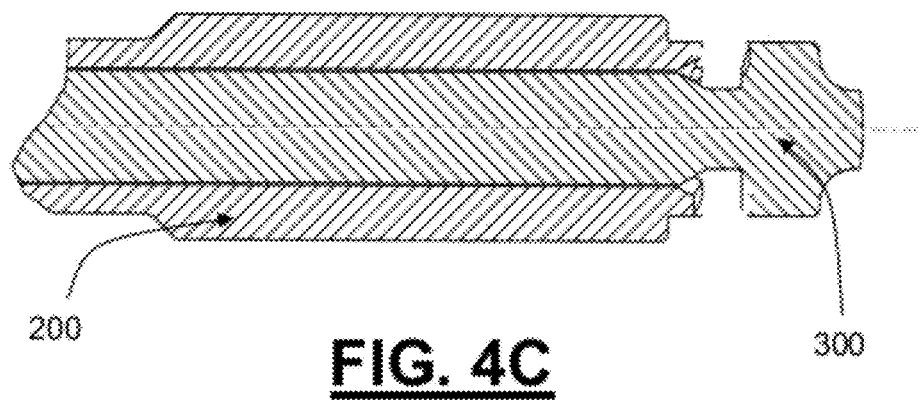
FIG. 4C is a partial cross-sectional view of the driven member and the stationary member of FIGS. 4A and 4B.

FIGS. 4A, 4B, and 4C are a (partial) three-dimensional view, side view, and cross-sectional view (respectively) of the driven member 300 and the stationary member 200 operatively coupled together in an intermediate state representative of several embodiments disclosed herein. As illustrated, the threaded portion (not shown) of the driven member 300 may be started in the hole in the bony structure, but the full axial depth has not yet been reached. In this condition, the driven member 300 is free to both rotate about and translate along its axis within the longitudinal hollow 212 of the stationary member 200.

Figure 5A:
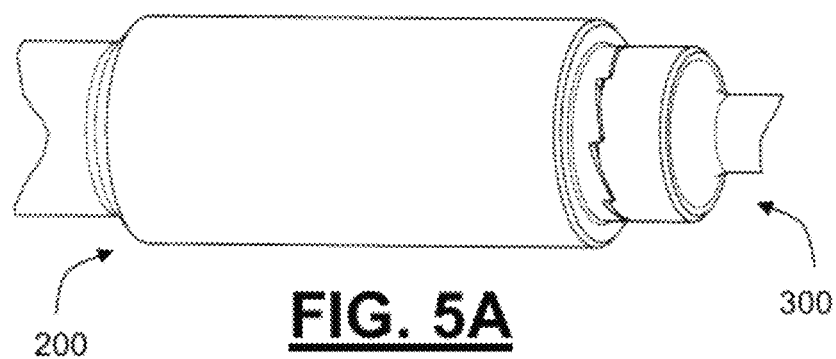
FIG. 5A is a partial three-dimensional view of the driven member and the stationary member operatively coupled together in a final locked state representative of several embodiments disclosed herein.
Figure 5B:
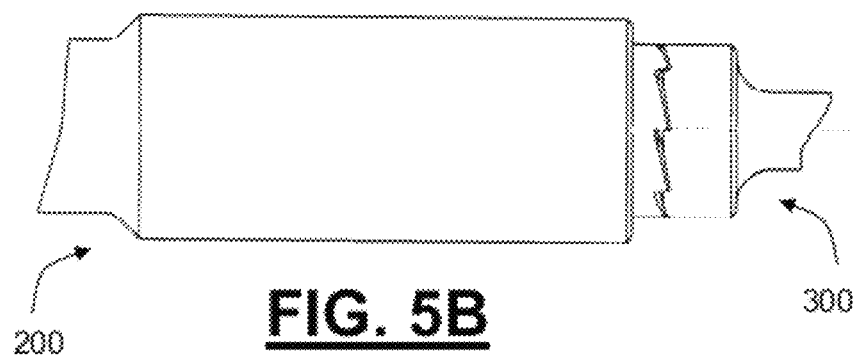
FIG. 5B is a partial side view of the driven member and the stationary member of FIG. 5A.
Figure 5C:
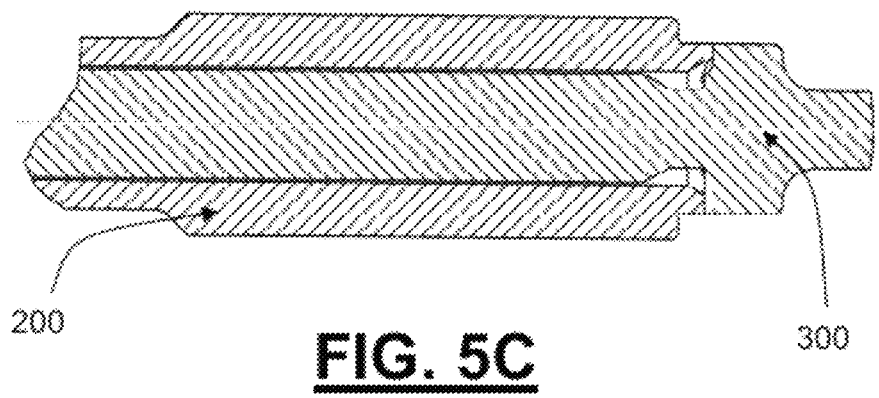
FIG. 5C is a partial cross-sectional view of the driven member and the stationary member of FIGS. 5A and 5B.

FIGS. 5A, 5B, and 5C are a (partial) three-dimensional view, side view, and cross-sectional view (respectively) of the driven member 300 and the stationary member 200 operatively coupled together in a final locked state representative of several embodiments disclosed herein. As illustrated, the threaded portion (not shown) of the driven member 300 has reached its final target depth. In this condition, the driven member 300 is both constrained from rotating in the clockwise direction and translating deeper into the stationary member 200. However, the driven member 300 is still free to rotate in the counterclockwise direction allowing it to back out of the stationary member 200.

Figure 6A:
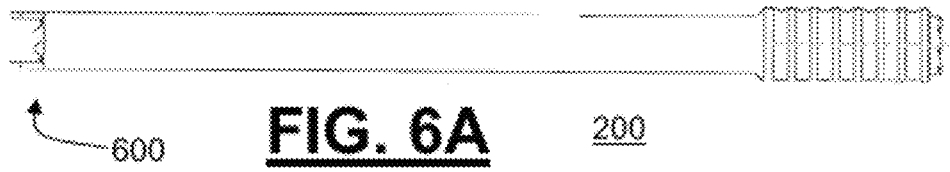
FIG. 6A is a side view of the stationary member comprising a distal anchoring mechanism representative of several embodiments disclosed herein.
Figure 6B:
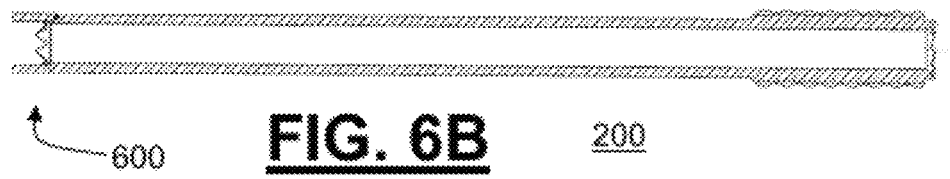
FIG. 6B is a cross-sectional view of the stationary member of FIG. 6A.

FIGS. 6A and 6B are a side view and cross-sectional view (respectively) of the stationary member 200 comprising a distal anchoring mechanism 600 representative of several embodiments disclosed herein. For certain embodiments, the distal anchoring mechanism 600 aids in maintaining the stationary member 200 stationary (and not rotating) at the point when a rotational force applied to the driven member 300 causes it to lock with the stationary member 300 in the final locked position as illustrated in FIGS. 5A, 5B, and 5C.

Figure 7:
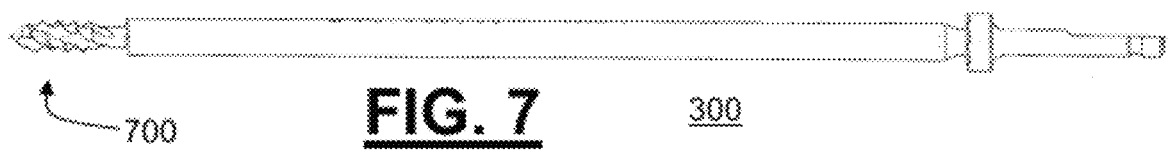
FIG. 7 is a side view of the driven member comprising a threaded tap at its proximal end representative of several embodiments disclosed herein.

FIG. 7 is a side view of the driven member 300 comprising a threaded tap 700 at its proximal end representative of several embodiments disclosed herein. This threaded tap 700 may be fixed or may be engaged in a coupling 800 illustrated in FIGS. 8A, 8B, and 8C.

Figure 8A:
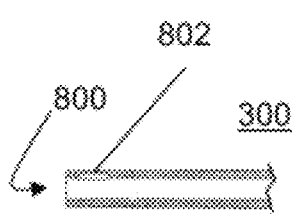
FIG. 8A is a partial side view of the distal end of a driven member featuring a coupling comprising a recess and a retention spring representative of several embodiments disclosed herein.
Figure 8B:
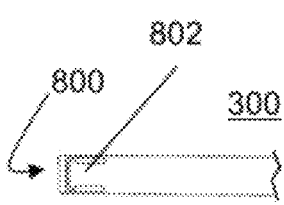
FIG. 8B is a top view of the driven member of FIG. 8A.
Figure 8C:
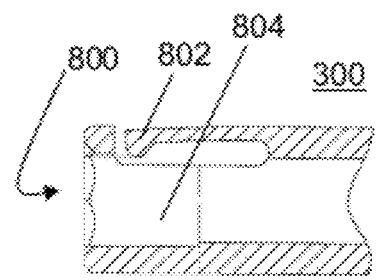
FIG. 8C is a close-up side cross-sectional view of the driven member of FIGS. 8A and 8B.

FIGS. 8A, 8B, and 8C are a (partial) side view, top view, and close-up side cross-sectional view (respectively) of the distal end of a driven member 300 featuring a coupling 800 comprising a recess 804 and a retention spring 802 representative of several embodiments disclosed herein. The recess 804 and retention spring 802 of the coupling 800 are provided in order to effectively mate with and retain a threaded component such as an allograft bony void filler or a synthetic implant, a threaded tap, or a drill bit.

Figure 9A:
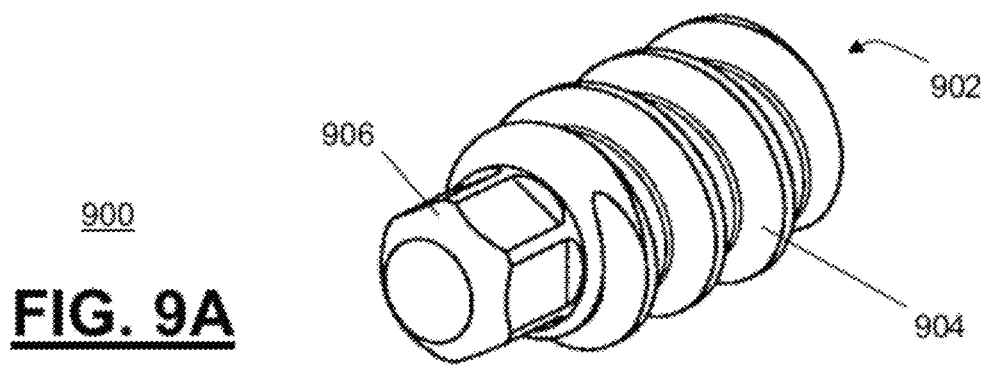
FIG. 9A is a three-dimensional view of a threaded allograft bony void filler that could be attached to the embodiment shown in FIGS. 8A, 8B, and 8C.
Figure 9B:
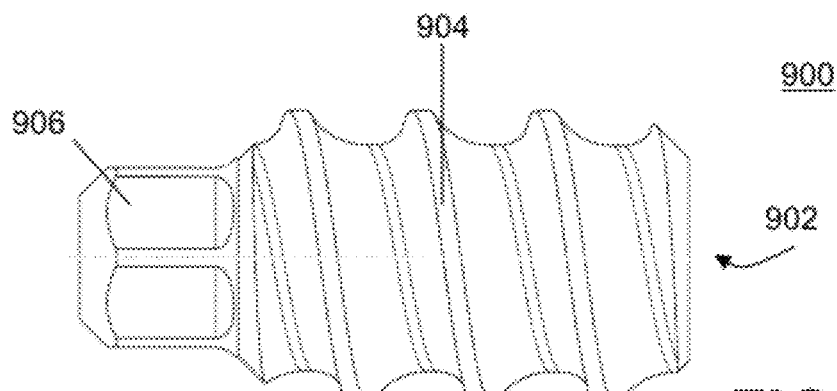
FIG. 9B is a side view of the threaded allograft bony void filler of FIG. 9A.
Figure 9C:
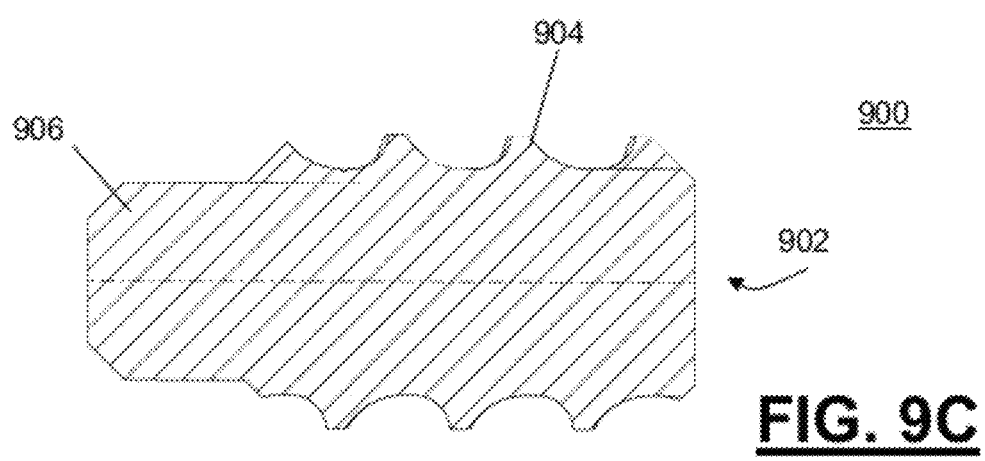
FIG. 9C is a close-up side cross-sectional view of the threaded allograft bony void filler of FIGS. 9A and 9B.

FIGS. 9A, 9B, and 9C are a three-dimensional view, side view, and cross-sectional view (respectively) of a threaded allograft bony void filler 900 that could be attached to the embodiment shown in FIGS. 8A, 8B, and 8C. The filler comprises a shaft 902 with threading 904 coupled to a drive feature 906.

Figure 10A:
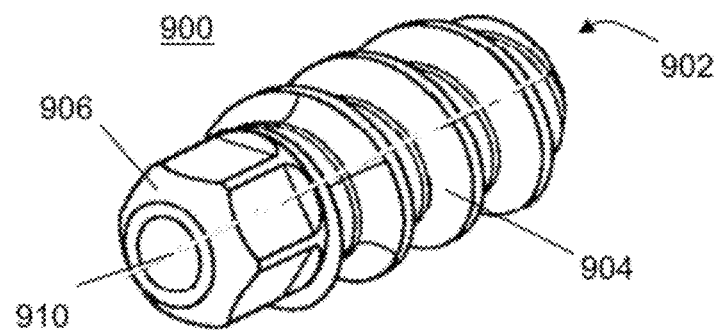
FIG. 10A is a three-dimensional view of the threaded allograft bony void filler of FIGS. 9A, 9B, and 9C further comprising a central channel.
Figure 10B:
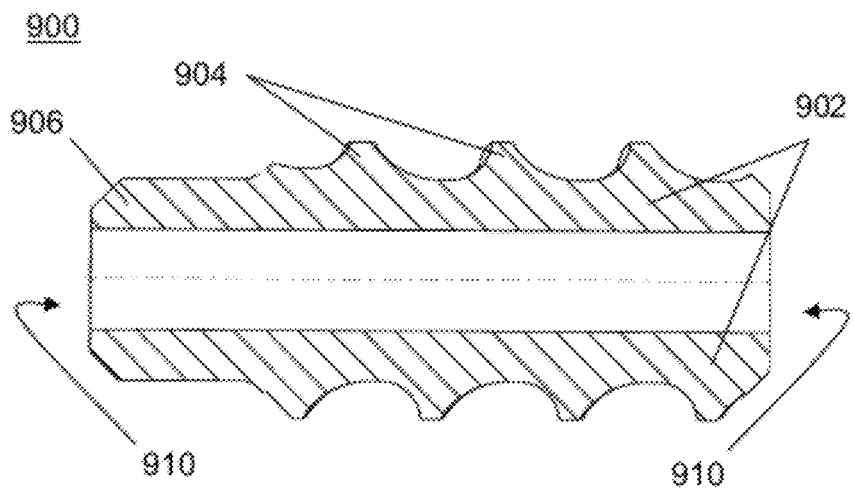
FIG. 10B is a side view of the threaded allograft bony void filler of FIG. 10A.
Figure 10C:
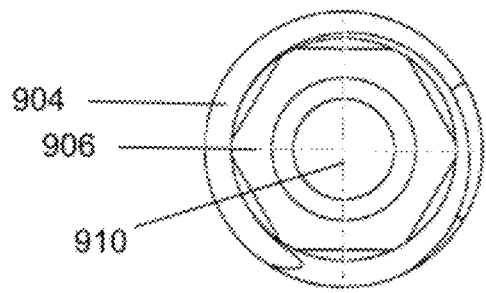
FIG. 10C is a close-up side cross-sectional view of the threaded allograft bony void filler of FIGS. 10A and 10B.

FIGS. 10A, 10B, and 10C are a three-dimensional view, side view, and cross-sectional view (respectively) of the threaded allograft bony void filler 900 of FIGS. 9A, 9B, and 9C further comprising a central channel 910 for use of a guide-wire or for another application.

Although FIGS. 9A, 9B, and 9C, as well as FIGS. 10A, 10B, and 10C, are directed to embodiments of a threaded allograft bony void filler, alternative embodiments directed to a synthetic implant of such are also contemplated. Moreover, any references herein this application to embodiments of a allograft dowels are also directed to similar alternate embodiments of synthetic implants, and vice versa, such that nothing herein shall deemed to describe embodiments of one without also describing similar embodiments of the other.

Figure 11:
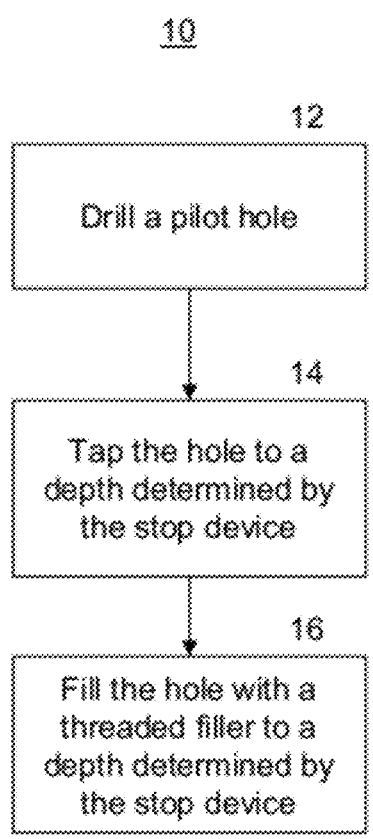
FIG. 11 is an operational flow diagram of a method for emplacing an allograft bony void filler or synthetic implant representative of several embodiments disclosed herein.

FIG. 11 is an operational flow diagram of a method 10 for emplacing an allograft bony void filler or synthetic implant representative of several embodiments disclosed herein. At 12 a pilot hole is drilled to a first depth, and this first depth may be predetermined by the use of a typical axial stop device that prevents axial advancement but does not restrict rotation (so that the drill bit may continue rotating even when a desired depth is reached in order to remove the debris). At 14 the pilot hole is tapped using an anti-rotation stop device to a second depth predetermined by the anti-rotation stop device. At 16 the allograft bone void filler or synthetic implant is used to fill the threaded hole using another (or the same) anti-rotation stop device to a third depth predetermined by the stop device. Without limitation, the first, second, and third depths may be the same or different depending on the desired depth for each operations, e.g., the first depth may be the greatest (deepest), followed by the second depth, followed by the third depth, or the second and third depth may be the same in some instances, such as when using the same anti-rotation stop device for both the tap and the filler or implant.

Moreover, in certain instances, the same stationary member 200 (of FIG. 2)—that may be used with the driven member 300 (of FIG. 3) for tapping, implantation, or both—can also be used for drilling when utilized with a drilling member that is similar to the driven member 300 but, in lieu of a mated toothed collar 304, having a smooth-surface collar that would act as an axial stop without preventing continued rotation of the drill bit. As such, the smooth-surface collar would abut against the high points of the mating toothed surface 204 of the stationary member 200 to prevent axial advancement but without interlocking with the proximal teeth 206 that instead rotationally slide against the smooth-surface collar.

It should be noted that for certain embodiments, the depth—and specifically, the distance from the posterior surface of the joint to the distal tip of the drill, tap, or allograft dowel—may be determined by two things: (a) the length of the stationary member 200 and (b) the distance from the stop collar to the distal tip on the driven member 300 (including coupled attachments for such embodiments). In other words, different depths can be achieved by varying the length of one or both of these members for each combination of a driven member and a stationary member. For example, for certain embodiments only the length of the driven members is varied while the length of the stationary member is standardized such that a single stationary member may be used for drilling, tapping, and filling/implanting in a surgical procedure.

The thread angle of the threads for the filler 900—as well as for a tap (not shown)—where the thread angle is measured as the angle from the longitudinal axis and the thread flank, should be no less than the angle of the pitched surface of the proximal and distal teeth of the stop device in order to ensure that the final lock occurs at the engagement of longitudinally-parallel surfaces of the teeth and not at the engagement of the pitched surfaces of the teeth (which could act as a wedge and, with rotational force, damage threads as discussed earlier herein).

For certain embodiments, the anti-rotation features (e.g., the stop device) could contain more or less than the eight teeth shown in the examples illustrated herein, depending on the allowable deviation in axial position for a given application, the angle of the pitched surface of the driven instrument or implant or graft, and/or the diameter of the components.

For certain embodiments, the teeth may be tilted (or raked) forward to encourage them to "lock" together to reduce slipping of the interface when large torques are applied. Similarly, for certain embodiments, the geometry of the teeth (e.g. the depth or angle of the cuts) could vary depending on the allowable deviation in axial position for a given application, the angle of the pitched surface of the driven instrument or implant or graft, and/or the diameter of the components.

For certain alternative embodiments, the roles of the tubular and cylindrical instruments (e.g., the stationary element 200 and the driven element 300, respectively) could be reversed so that the tubular instrument is the driven instrument and the cylindrical instrument is the stationary instrument. And again, for other alternative embodiments, the direction of the teeth could be reversed to prevent counterclockwise rotation for left-handed threads.

In some embodiments, the anti-rotation interface may be used to create a simple ratcheting drive mechanism to allow a fastener or other threaded member to be driven in discreet angular increments without having to substantially disengage the driver from the driven component. In some other embodiments, the anti-rotation interface could be used as a tamper-proof drive interface between a driver and a threaded component to allow a user to drive the component in one direction but not the other. In yet other embodiments, the anti-rotation interface could be used in a coupling application where relative rotary motion between coaxial components is permitted in one direction but not in the reverse direction to prevent damage to a drive train due to reversing torques on the output (driven) component. In addition, for several alternative embodiments the anti-rotation features and/or their respective instruments could be made from any metallic, polymeric, or composite material that is suitable for use in surgical applications (e.g. stainless steel, titanium, titanium alloys, PPSU, PEEK or carbon-fiber reinforced epoxy, and so forth).

The subject matter described above is provided by way of illustration only and should not be construed as limiting. Various modifications and changes may be made to the subject matter described herein without following the example embodiments and applications illustrated and described, and without departing from the true spirit and scope of the present invention, which is set forth in the following claims.

What is claimed is:

1. An axial and rotational stop device comprising:
a single stationary member comprising a first mating toothed surface, wherein said first mating toothed surface comprises teeth with a longitudinal surface and a pitched surface; and a driven member comprising a second mating toothed surface, wherein said second mating toothed surface comprises teeth with a longitudinal surface and a pitched surface;
wherein the driven member is prevented from axially advancing and rotating in a first direction, and allowed to rotate in the opposite direction, when the first mating toothed surface engages the second mating toothed surface, and further wherein the stationary member comprising the first mating toothed surface further comprises a hollow shaft, and further wherein the driven member comprising the second mating toothed surface further comprises a collar, and
wherein the driven member comprises a solid insertion shaft for insertion through the hollow shaft and the first mating toothed surface, the insertion shaft having a first diameter tapering to a second, lesser, diameter adjacent the collar.

2. The device of claim 1 wherein the driven member further comprises a tap for threading a pre-drilled hole to a predetermined depth.

3. The device of claim 1 wherein the driven member further comprises:
a coupling engaging a tap or a threaded component, and
a retention spring to retain the tap or the threaded component respectively.

4. The device of claim 3 wherein the tap component and the threaded component are a same longitudinal length and can be joined with the driven member via the coupling.

5. The device of claim 1 wherein the stationary member comprises a distal anchoring mechanism.

6. The device of claim 1 wherein the driven member is allowed to axially withdraw by rotating in a second direction opposite the first direction even when the first mating toothed surface engages the second mating toothed surface.

7. The device of claim 1 wherein the first mating toothed surface and the second mating toothed surface comprise raked teeth.

8. The device of claim 1 wherein the driven member is allowed to axially rotate in the opposite direction using clockwise rotation and right-handed threads.

9. The device of claim 1 wherein the driven member is allowed to axially rotate in the opposite direction using counterclockwise rotation and left-handedthreads.

10. The axial and rotational stop device of claim 1, wherein the first diameter of the insertion shaft is along a majority of the length of the insertion shaft.

11. The axial and rotational stop device of claim 1, wherein the hollow shaft includes a central through-hole extending therethrough, a proximal end of the central through-hole having a tapered surface such that a diameter of a proximal opening of the hollow shaft is greater than a diameter of the central through-hole.

12. A threaded filler apparatus comprising:
a single stationary element comprising:
a hollow shaft having a longitudinal hollow; and
a mating toothed surface coupled to the hollow shaft, said mating toothed surface comprising a plurality of proximal teeth, wherein said proximal teeth comprise a longitudinal surface and a pitched surface; and
a driven element comprising:
a solid insertion shaft of the driven element extending through the longitudinal hollow and the first mating toothed surface; and
a mating toothed collar coupled to the solid insertion shaft, the solid insertion shaft having a first diameter tapering to a second, lesser, diameter adjacent the mating toothed collar, wherein said mating toothed collar comprising a plurality of distal teeth to engage the proximal teeth, wherein said distal teeth comprise a longitudinal surface and a pitched surface; wherein the driven element is prevented from axially advancing and rotating in a first direction, and allowed to axially rotate in the opposite direction.

13. The apparatus of claim 12 wherein the stationary element further comprises a distal anchor to prevent rotation of the stationary element when the proximal teeth engage the distal teeth.

14. The apparatus of claim 12 wherein the driven element further comprises a coupler at its distal end to mate with a tool from among the following plurality of tools: a drill bit, a tap, and a filler.

15. The apparatus of claim 14 wherein the filler comprises threads with a thread angle.

16. The threaded filler of claim 12, wherein the first diameter of the insertion shaft is along a majority of the length of the insertion shaft.

17. The threaded filler of claim 12, wherein the longitudinal hollow comprises a proximal end having a tapered surface such that a diameter of a proximal opening of the hollow shaft is greater than a diameter of the longitudinal hollow.

* * * * *